United States Patent
Kantzas et al.

(10) Patent No.: US 6,399,390 B1
(45) Date of Patent: Jun. 4, 2002

(54) MEASURING MOVEMENT OF SOLID PARTICLES AND PARTICLE INTERACTIONS IN A FLOWING SYSTEM

(75) Inventors: Apostolos Kantzas; Kelly Hamilton; Tanghi Zarabi; Ian Wright, all of Calgary (CA)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 09/548,002

(22) Filed: Apr. 12, 2000

(51) Int. Cl.[7] ............................................. G01N 23/083
(52) U.S. Cl. ..................... 436/57; 436/56; 250/356.2; 250/358.1; 250/363.01
(58) Field of Search ...................... 436/56, 57; 250/362, 250/363.01–363.04, 356.2; 73/53.01, 861.05, 861.07, 861.41

(56) References Cited

PUBLICATIONS

Paper "Application of Gamma Camera Imaging and SPECT Systems in Chemical Processsse" 1st World Congress on Industrial Tomography, Buxton, Greater Manchester, Apr. 14–17, 1999.

*Primary Examiner*—Jill Warden
*Assistant Examiner*—Yelena Gakh (57) ABSTRACT

A method of measuring the movement of solid particles and particle interactions in a flowing system includes the step of providing two gamma cameras set up at right angles to each other to periodically record the position of a radioactively tagged particle in the flowing system. Probability distribution functions, particle positions, particle velocities, amongst other useful information, may be determined from the camera data.

6 Claims, 12 Drawing Sheets

MEASURING MOVEMENT OF SOLID PARTICLES AND PARTICLE INTERACTIONS IN A FLOWING SYSTEM

FIELD OF THE INVENTION

The present invention relates to a method of measuring movement of solid particles and particle interactions in a flowing system. In particular, the invention relates to radioactive particle tracking within a chemical reactor.

BACKGROUND OF THE INVENTION

The introduction of new computational fluid dynamics ("CFD") models describing flow phenomena in chemical reactors offers information including voidage maps, pressure distribution maps and particle velocity maps as a function of position and time and in two or three dimensions. Such models can be used for predicting hydrodynamics in the reactor. However, there is very little direct verification of all these maps, making the applicability of such models dubious. One way to validate such models is to perform simulations using laboratory or pilot plant scale reactors equipped with a variety of sensors that can measure reactor properties. These properties usually include local pressure and temperature measurements, superficial fluid flow rate measurements and localized measurements of bubble imaging through intrusive probes.

It would be advantageous to possess techniques to measure reactor properties without intrusive probes to provide multi-dimensional information of properties similar to those predicted by computational fluid dynamics and to verify those predictions. Such techniques may then be used to calibrate CFD models and apply them as tools for scale-up predictions.

SUMMARY OF THE INVENTION

The present invention provides for methods of measuring movement of solid particles and particle interactions in a three-dimensional flowing system. Such methods are useful for predicting and verifying the hydrodynamic behaviour of flowing systems which allows one skilled in the art to design or modify flowing systems to enhance their efficiency or to suit a particular purpose.

In one aspect of the invention, said method comprises the steps of:
(a) providing at least one radioactive tagged particle within the flowing system;
(b) providing at least one image receptor capable of detecting the position of the tagged particle in the x-z plane; and
(c) periodically recording the position of the tagged particle in the x-z plane over a length of time.

In a preferred embodiment, the method further comprises the steps of providing a second image receptor capable of detecting the position of the tagged particle in the y-z plane and periodically recording the position of the tagged particle in the y-z plane at the same times the first image receptor records the position of the tagged particle in the x-z plane. The first and second image receptors may be gamma cameras and the particle may be tagged with radioactive technetium.

BRIEF DESCRIPTION OF THE DRAWINGS

The invention will now be described with reference to the accompanying drawings in which.

DETAILED DESCRIPTION OF THE INVENTION

The present invention provides for methods of measuring movement of solid particles and particle interactions in a flowing system. In particular, the invention relates to radioactive particle tracking within a chemical reactor. All examples presented involve a fluidized bed reactor, however one skilled in the art may extend the methods of the present invention to other flowing systems or chemical reactors. When describing the present invention, the following terms have the following meanings, unless indicated otherwise. All terms not defined herein have their common art-recognized meanings.

A. Definitions

The term "chemical reactor" refers to any vessel within which a chemical reaction occurs. The reactants, catalysts and/or products of interest may be gases, liquids or solids.

The term "flowing system" refers to any chemical process mixture that flows under a pressure gradient.

The term "fluid bed" or "fluidized bed" refers to a multi-phase system that includes a solid and a fluid mixture. The solids of the mixture are not stationary rather they flow within the system.

B. Description

In the following description, the chemical reactor, flowing system or fluidized bed will be described in three dimensions where the "z" axis is vertical and the "x" and "y" axes are horizontal. Therefore, the "y-z" plane and the "x-z" plane are vertical and at right angles to each other.

A radioactive particle may be tracked within a flowing system or fluidized bed by using a gamma camera system. The fluidized bed is placed in front of one gamma camera and preferably two gamma cameras, where one camera records events in the "y-z" plane and the other simultaneously records events in the "x-z" plane so that information in three dimensions may be obtained. Of course, the cameras may be placed along any two planes that are normal to each other to obtain three dimensional information. The choice of the "y-z" plane and the "x-z" plane is for convenience.

Alternatively, three dimensional information may be obtained by computed tomography techniques using a single camera which physically orbits the object of interest, taking a series of static images at different angles. Reconstruction algorithms may then be used to assimilate all the two dimensional images from which tomographic slices can be made at any level and in any direction. Such reconstruction algorithms are available in commercially available medical imaging softwares.

Gamma camera systems are well known and commercially available. The results obtained in the examples given below were obtained with either a Siemens® Orbiter model or a Siemens® ZLC. Each model has 75 photomultiplier tubes and a NaI(TI) crystal with a diameter of 41 cm.

The cameras record the position of a tracer particle which has been formed to be the same as the other particles in the fluidized bed except that the tracer particle is tagged radioactively. The tracer particle emits gamma rays which are detected by the gamma cameras. It is important that the tracer particle be identical to the other particles in the fluidized bed so that its movement and interaction with other particles is representative of the average particle. The radioisotope may be chosen from radioisotopes conventionally used in nuclear medicine. In a preferred embodiment, technetium ($^{99m}$Tc) is used because of its availability, cost effectiveness, energy of emission and short physical half life. The radioisotope may be chelated to be then incorporated into the tracer particle. In one embodiment, macroaggregated albumin is used to chelate the radioisotope. The radiolabeled protein may be incorporated into the tracer particle by mixing the protein with a molten slug of the particle, such as molten polyethylene, which is then allowed to cool and harden. A particle identical to a typical bed particle may then be fashioned from the radioactive pellet. Alternatively, the radio isotope can be attached to the particle through ion-exchange, precipitation, agglomeration or deposition with a physical glue.

The following examples are exemplary of the claimed invention and are not intended to be interpreted as limiting of the invention in any manner. In each example, the flowing system analyzed was a gas-solid fluidized bed contained in an annular container. In each example, both cameras were started at the same time manually. The images were then synchronized by finding the time lag between the two cameras using auto-correlation and adjusted accordingly. The images were clipped at the beginning and end of acquisition so as to have meaningful 3 dimensional data. All the images showed good contrast and were acquired at the rate of 5 Hz. Initial tests were done to determine the optimum frequency of acquisition. Optimum sampling frequency is determined by particle size and particle activity and may range from 1 Hz to 1000 Hz. The particle was doped with $^{99m}$Tc. The particle had sufficient radioactivity to penetrate surrounding media, water, glass and was easily distinguishable from the background radiation. A resolution of 3.2 mm was obtained. Typical particle activities should exceed 1500 counts per second but may be lower.

The images were processed by determining the number of counts per pixel. Background radiation was subtracted and the scattering around the particle was eliminated. The centre of the radioactive particle was calculated through a center of mass calculation. When this was done the coordinates of the particle were recorded. From the particle coordinates in sequential frames, the axial and radial velocities of the particle were also calculated. When all the coordinates and all the velocities were calculated, the results were tabulated and plotted using spreadsheets. Furthermore, the data provided frequency distributions for velocity components and probability density functions for the particle location within the bed. Additional calculations may be performed to provide local time averaged velocities, azimuthally averaged velocities, fluctuating velocities, intensity of turbulence terms, normal and shear stress terms, turbulent kinetic energy and turbulent dispersion coefficients.

FIG. 1 to FIG. 6 show results depicting particle positioning and movement obtained from radioactive particle tracking experiments conducted at various superficial velocities. Ten sets of images for each superficial velocity were acquired amounting to 10,000 frames, each frame lasting for a duration of 200 ms, which is about 30 minutes of real time data for each superficial velocity. Since each of these 10 sets of data for a particular velocity were collected over two hours of experimental time, the results represent the time averaged quantities in the bed and give a representative picture with an insight into the hydrodynamic behavior of the fluidized bed.

Figure 1:
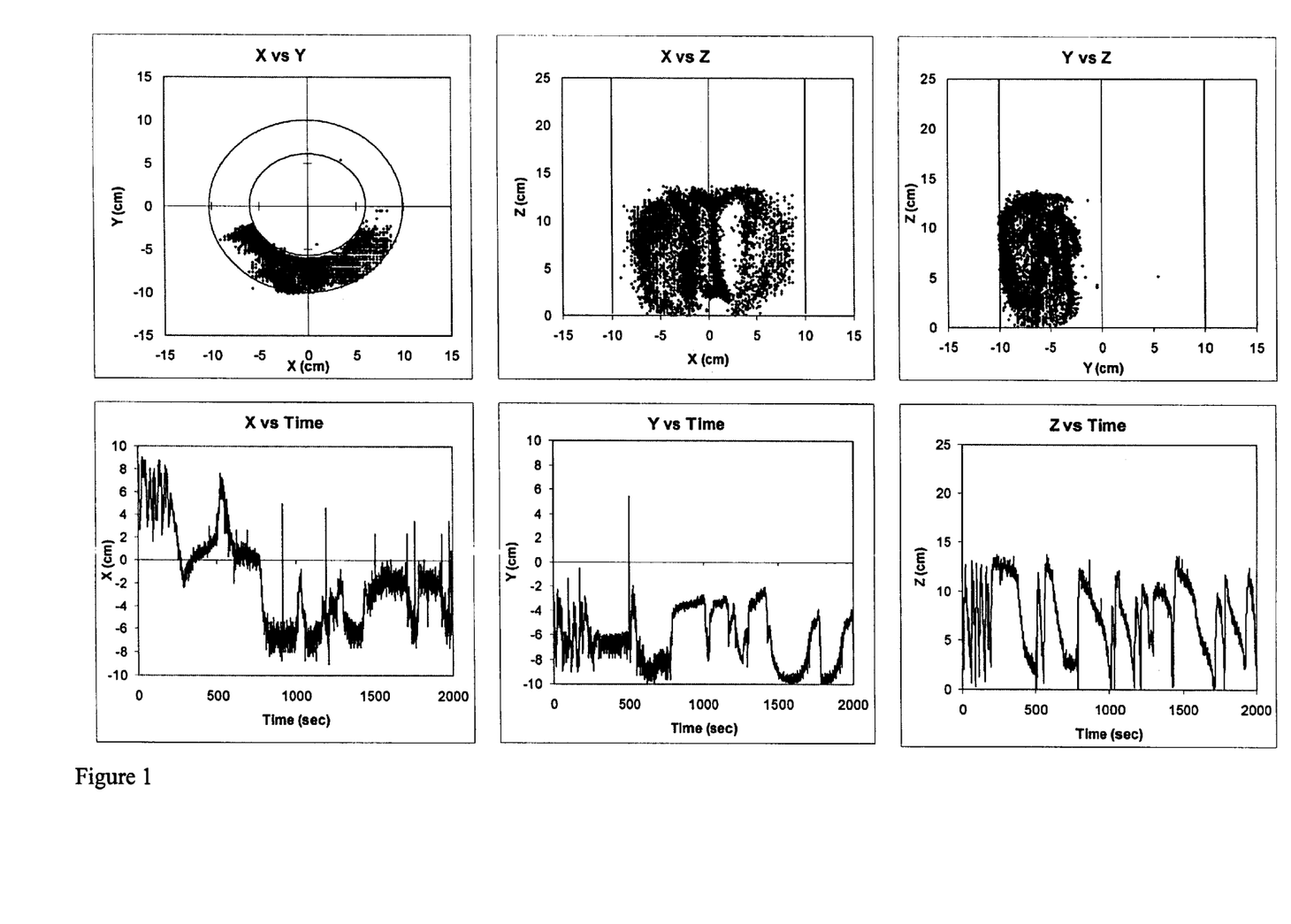
FIG. 1 shows particle positioning and particle trajectories for a fluidized bed where superficial velocity=0.66 cm/s
Figure 2:
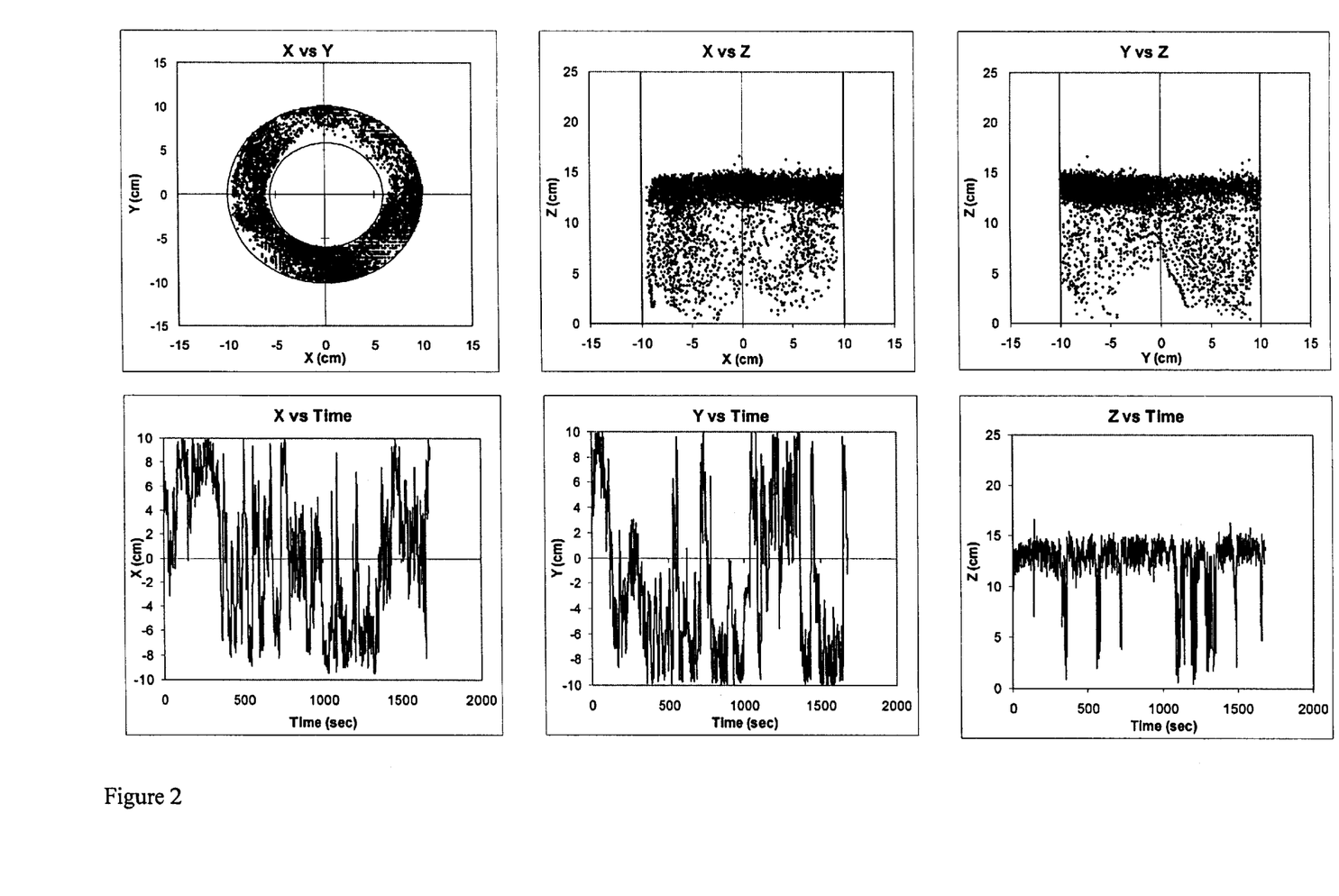
FIG. 2 shows particle positioning and particle trajectories for a fluidized bed where superficial velocity=1.00 cm/s
Figure 3:
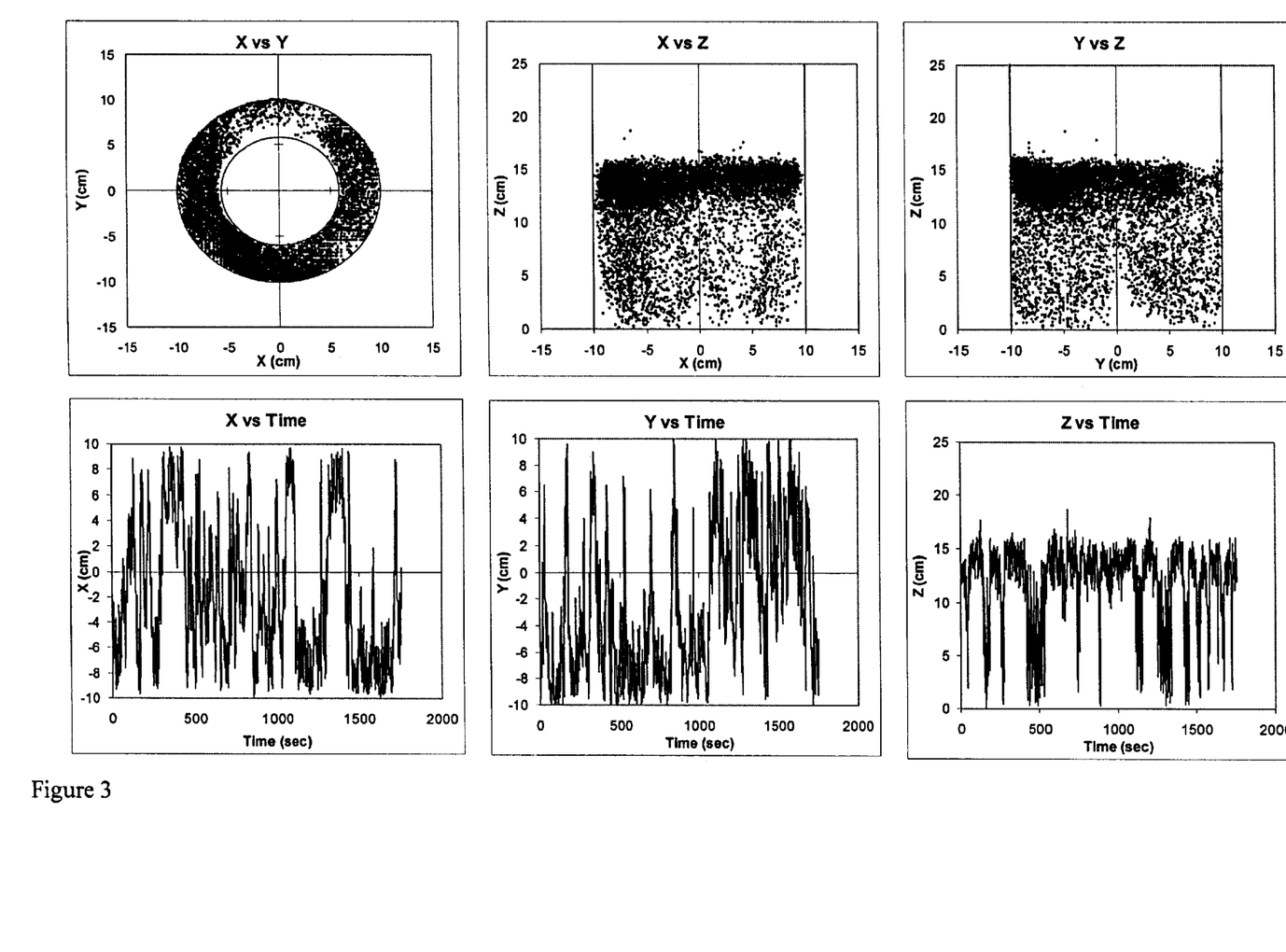
FIG. 3 shows particle positioning and particle trajectories for a fluidized bed where superficial velocity=1.33 cm/s
Figure 4:
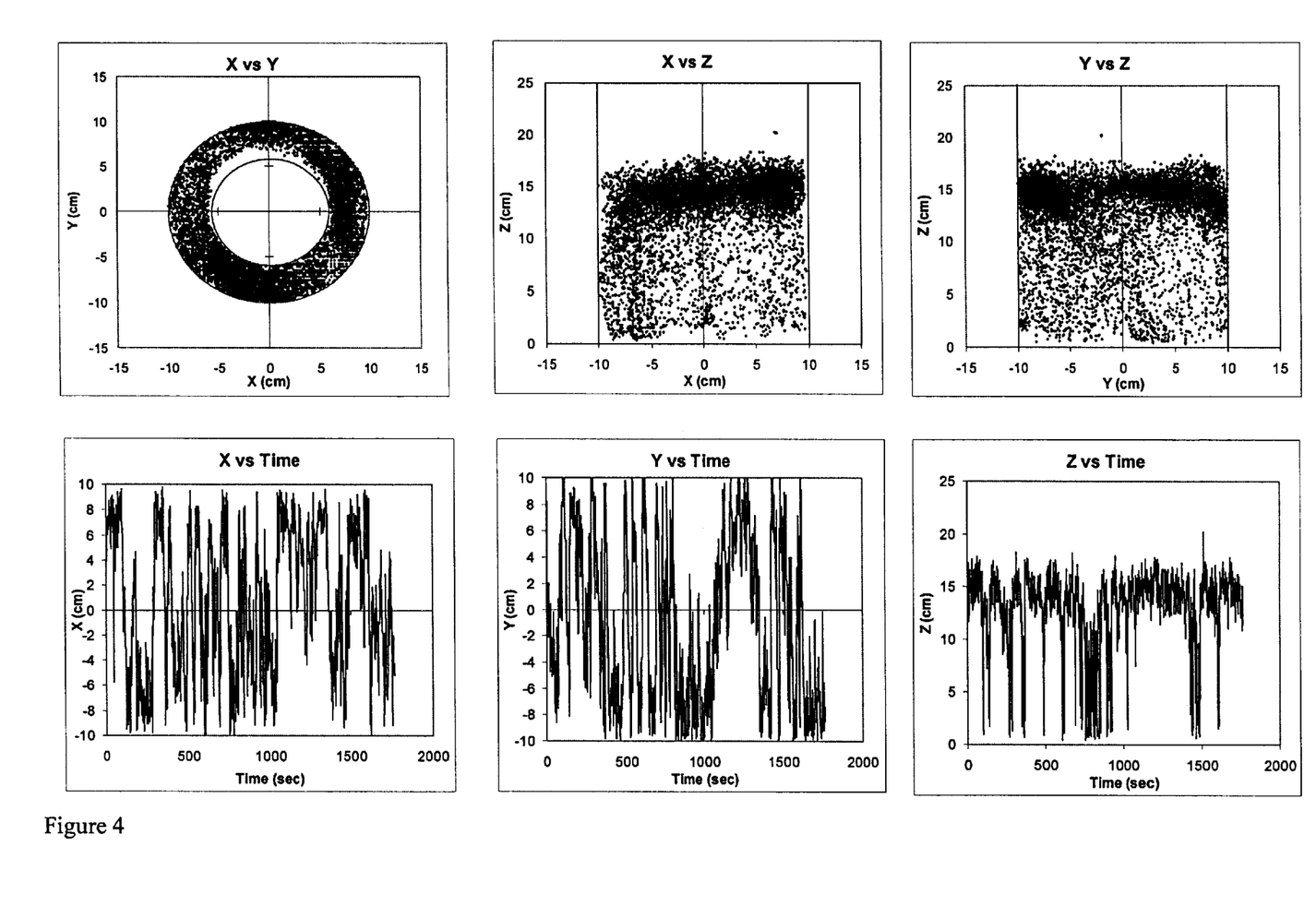
FIG. 4 shows particle positioning and particle trajectories for a fluidized bed where superficial velocity=1.66 cm/s
Figure 5:
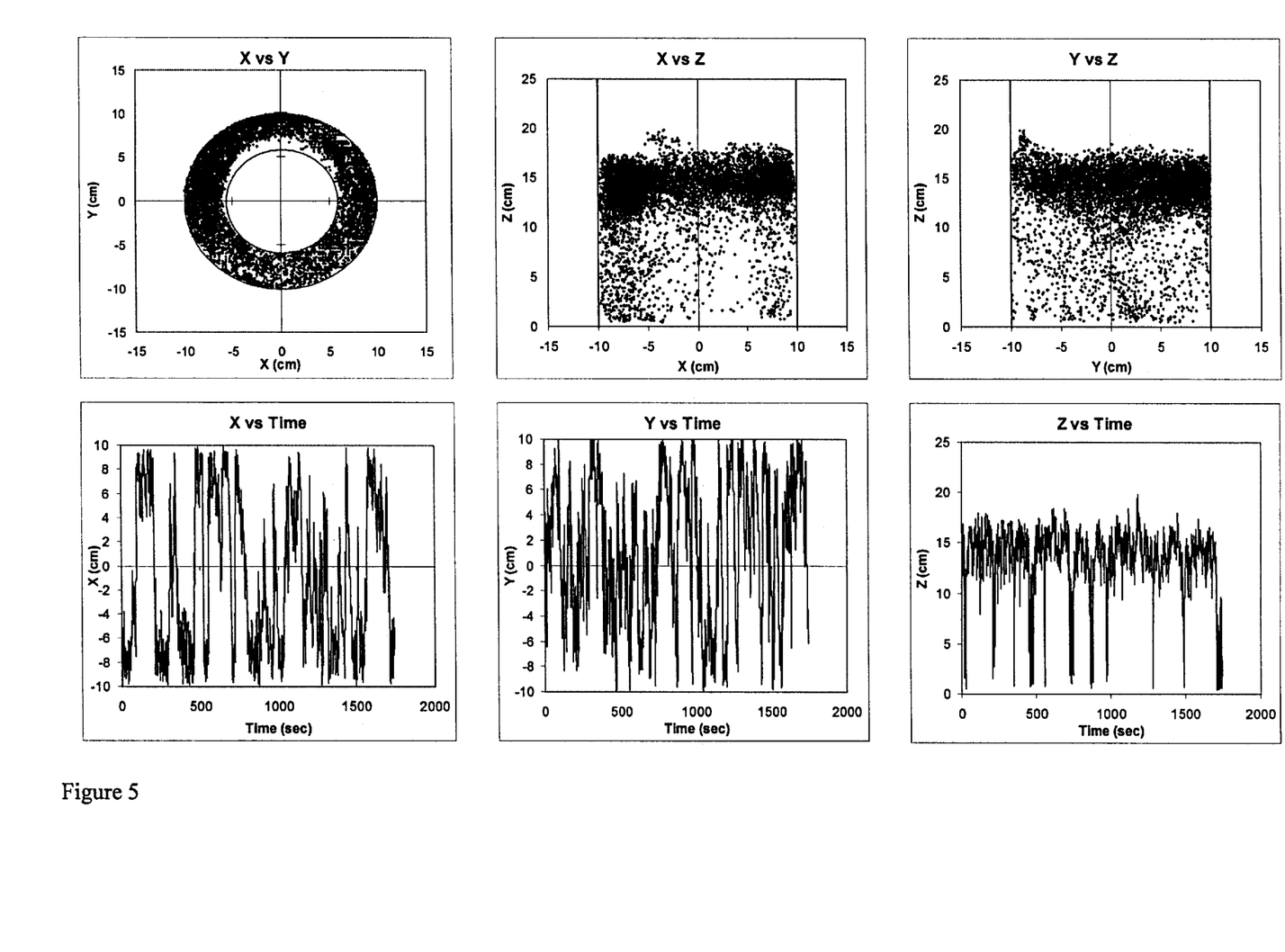
FIG. 5 shows particle positioning and particle trajectories for a fluidized bed where superficial velocity=2.00 cm/s
Figure 6:
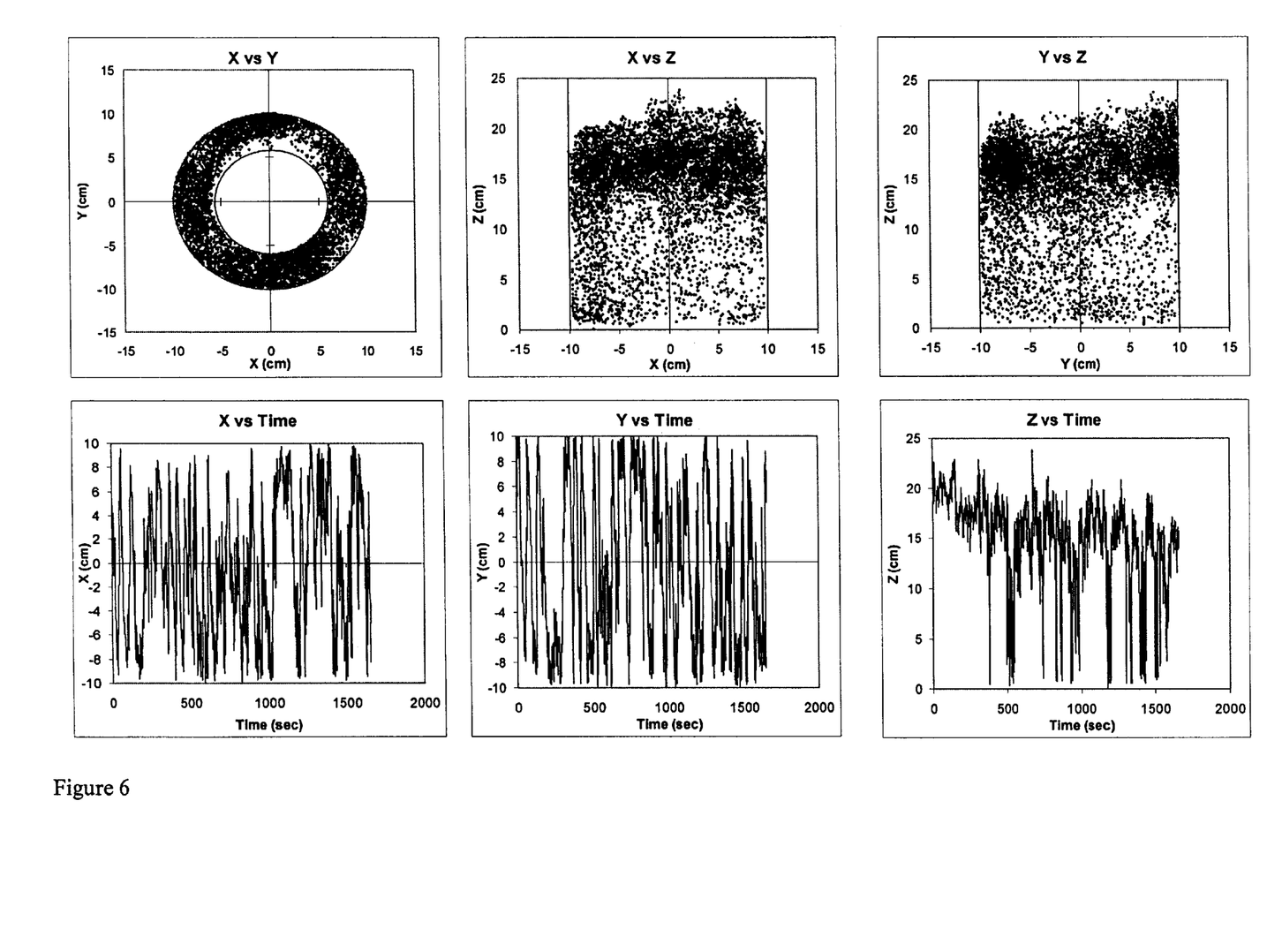
FIG. 6 shows particle positioning and particle trajectories for a fluidized bed where superficial velocity=2.32 cm/s

Each of the FIGS. 1 to FIG. 6 display particle positioning and particle trajectories in x, y and z directions. FIG. 1 corresponds to images acquired at 0.66 cm/s superficial velocity, which is below the minimum fluidization velocity for this reactor. Localized movement of particle was observed when it was caught up in the jets near the distributor. In this case, there was very poor mixing and particle movement was restricted to a small area.

Increasing the superficial velocity leads to better mixing, fewer dead zones, and particle visiting everywhere as is evident from FIGS. 2 to 6. However, it was observed that the particle spent more time in the freeboard region than in other parts of the bed. This may be attributed to the fact that the chosen particle was doped with radioactive material using glue and since glue is lighter than the material of the fluidized bed, it might have resulted in a slightly lighter radioactive particle. Another reason for this behaviour could be that the specific particle chosen to be tracked may have been lighter or smaller than the rest of fluidized bed particles.

Figure 7:
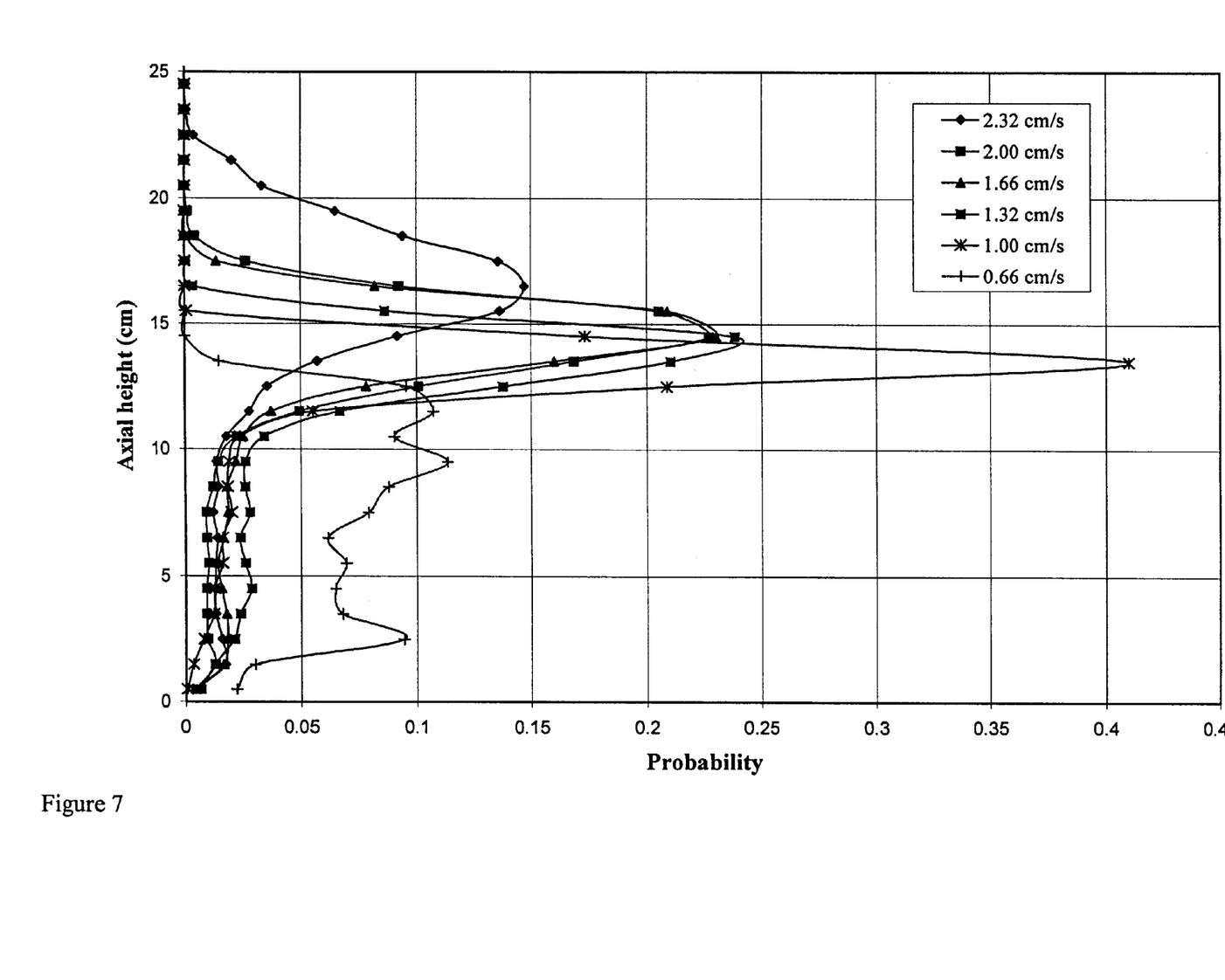
FIG. 7 shows the probability distribution function of particle occurrence in the bed with respect to bed height.
Figure 8:
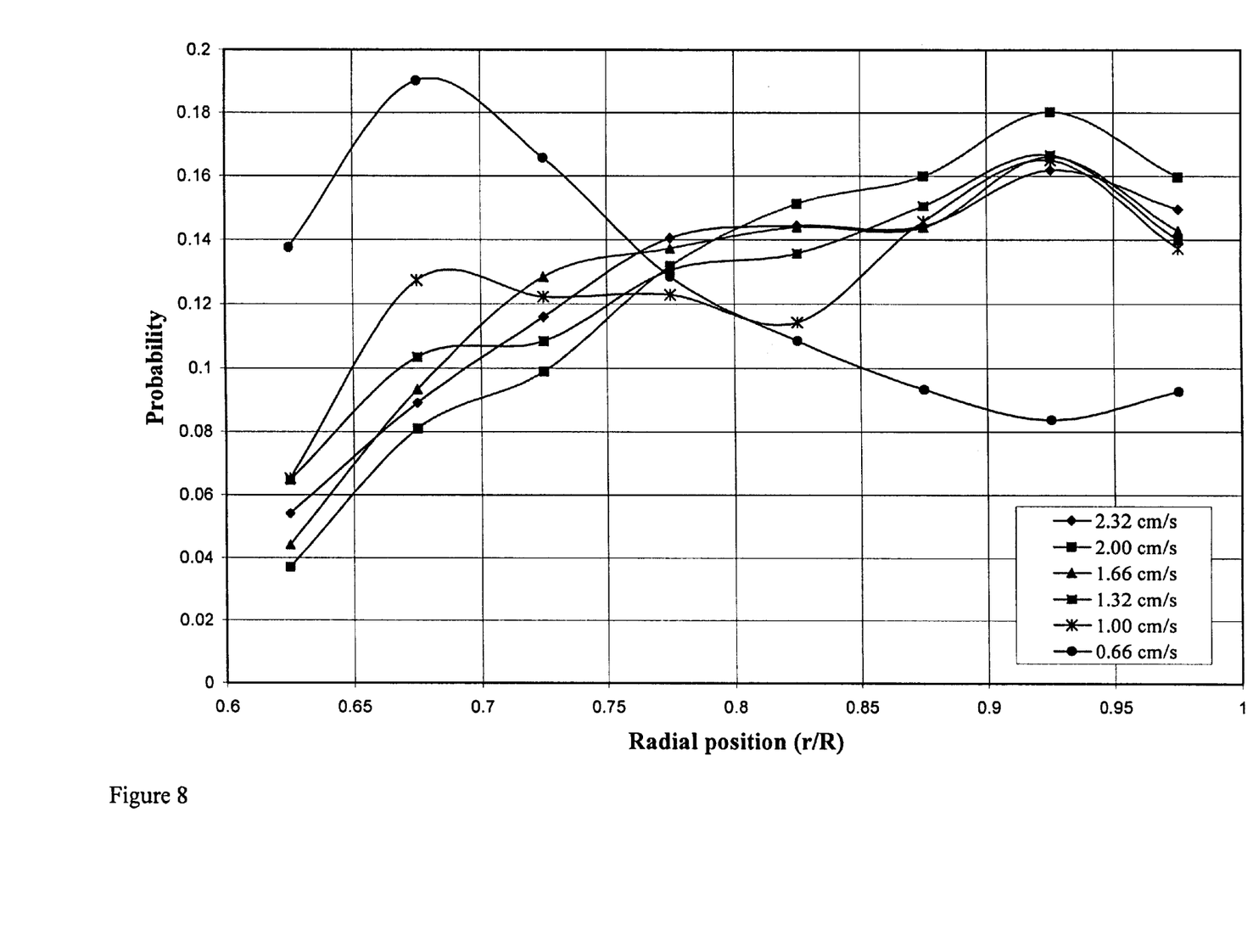
FIG. 8 shows the probability distribution function of particle occurrence in the bed with respect to radial position.

FIGS. 7 and 8 show the probability distribution function (PDF) of particle occurrence in the bed at the same conditions as discussed above. These plots were obtained by dividing the bed into many compartments of known sizes and computing the number of particle occurrences (particle visiting times) in each compartment. It is evident that the particle visited everywhere in the bed. In the top part or freeboard region of the bed, the PDF of particle occurrence seems higher than the bottom part implying that the particle stayed longer in this part. All the curves are similar in nature beyond the minimum fluidization velocity. However, at superficial velocity of 0.66 cm/s, both FIGS. 7 and 8 show a drastically different curve. From FIG. 8, we can notice the wall effect, the PDF at various superficial velocities drops down very close to the outside and inside walls. As we go away from the inside wall, PDF increases steadily for all superficial velocities above minimum fluidization and then decreases when we reach the outer wall of the bed container.

Figure 9:
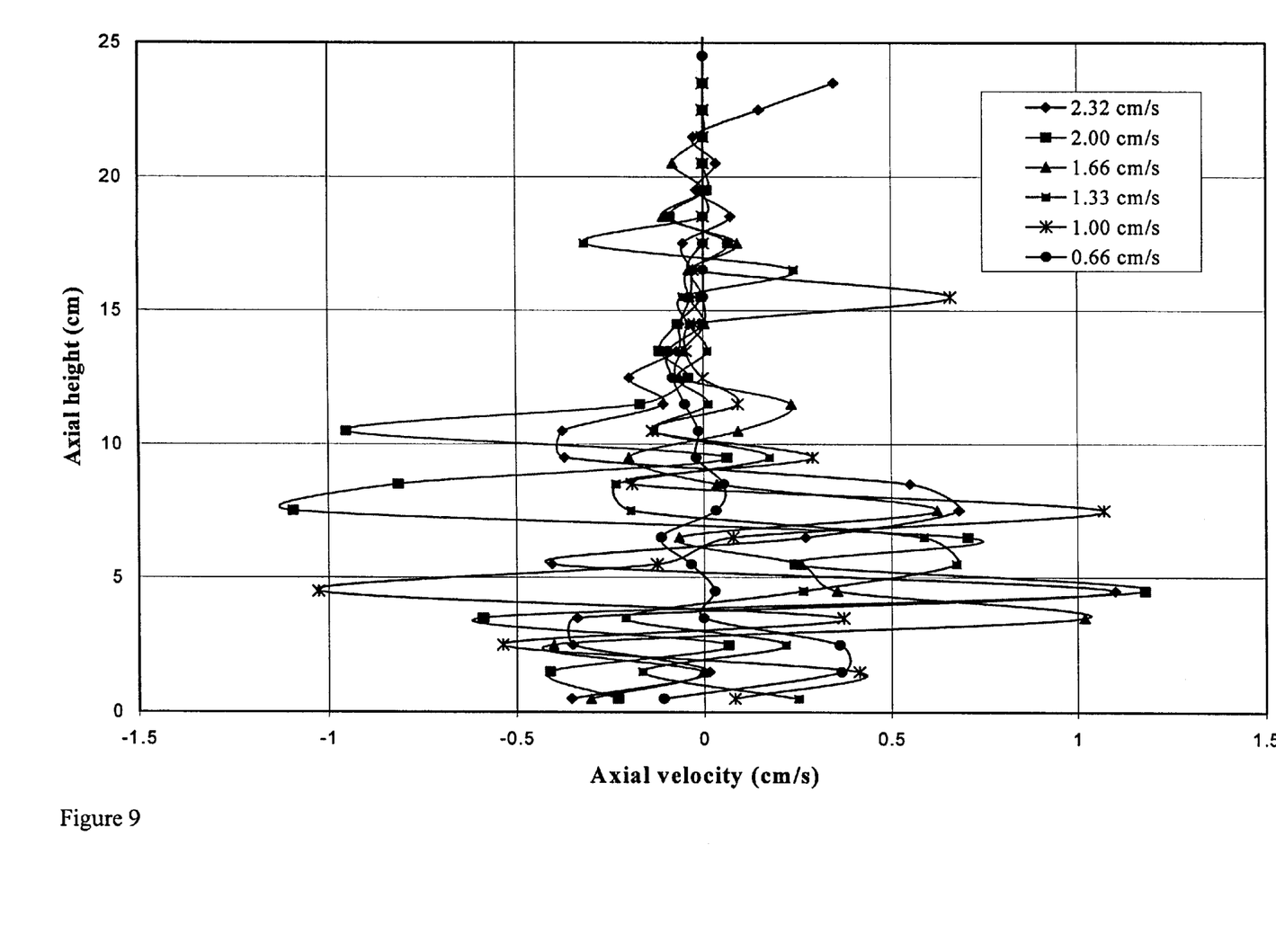
FIG. 9 shows the axial component of particle velocity as a function of axial bed height.
Figure 10:
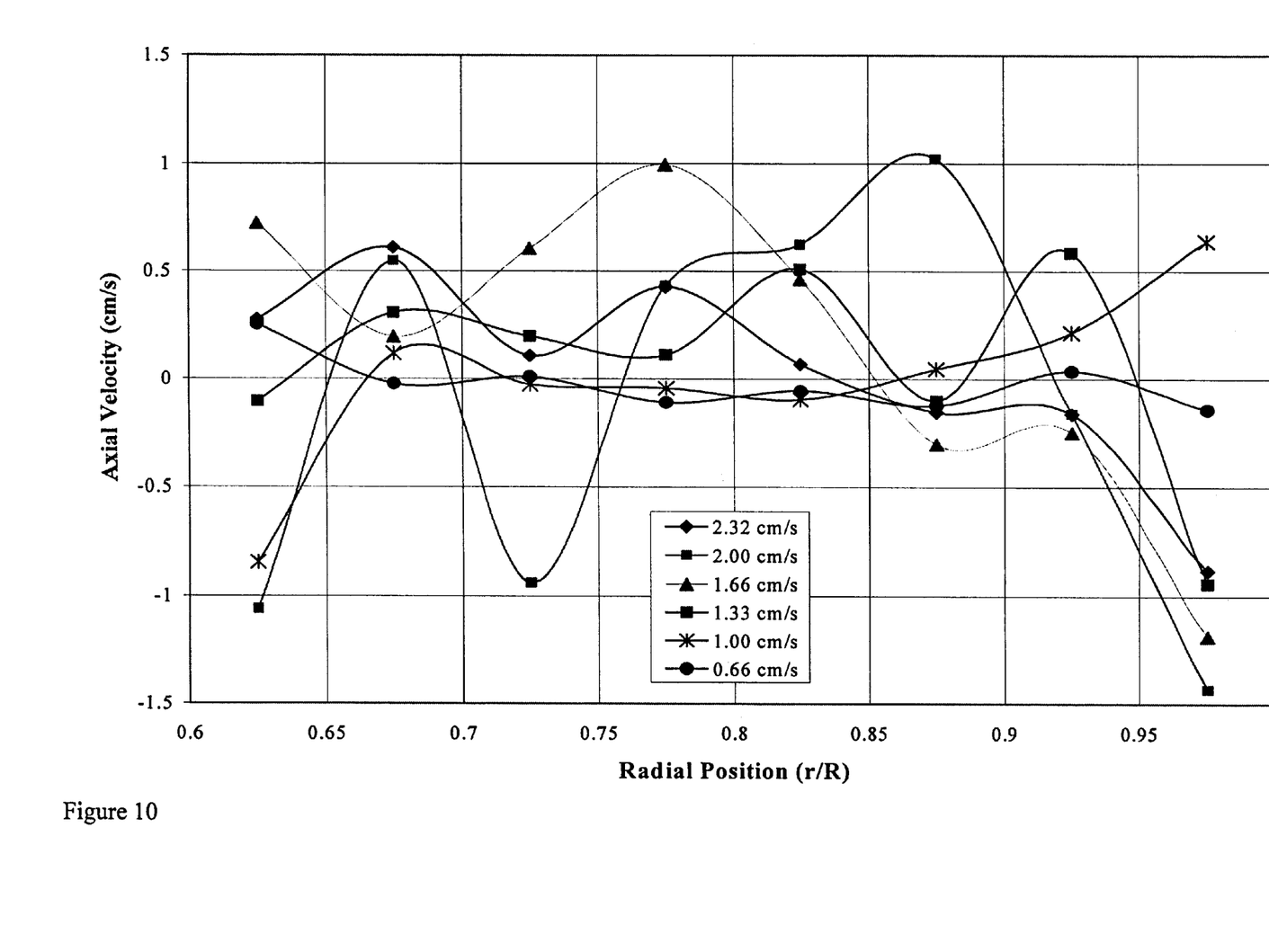
FIG. 10 shows the axial component of particle velocity as a function of radial position.

FIGS. 9 and 10 show the axial velocity component of the particle as a function of axial and radial position, respectively. In the former, the radial velocity component is a mean of velocity component in all compartments at the same axial bed height and in the latter case, axial velocity component is a mean of velocity component in compartments equidistant from the centre. All the axial components of particle velocities range from −1.50 to 1.50 cm/s which is less than the superficial gas velocities indicating the presence of particle-particle interactions which are slowing the particle down. FIG. 9 indicates that there is a higher oscillatory motion with higher velocities in the fully developed flow region of the bed. The axial component of particle velocity first increases as the bed height increases and then drops down to very low velocities in the freeboard region. The magnitude of velocities increases with the increasing superficial velocities. FIG. 10 depicts the variation in axial velocity component along the radius of the reactor. In general, the results in these examples demonstrate that the particle rises in the core i.e. away from the walls and falls down near the inner and outer walls.

Figure 11:
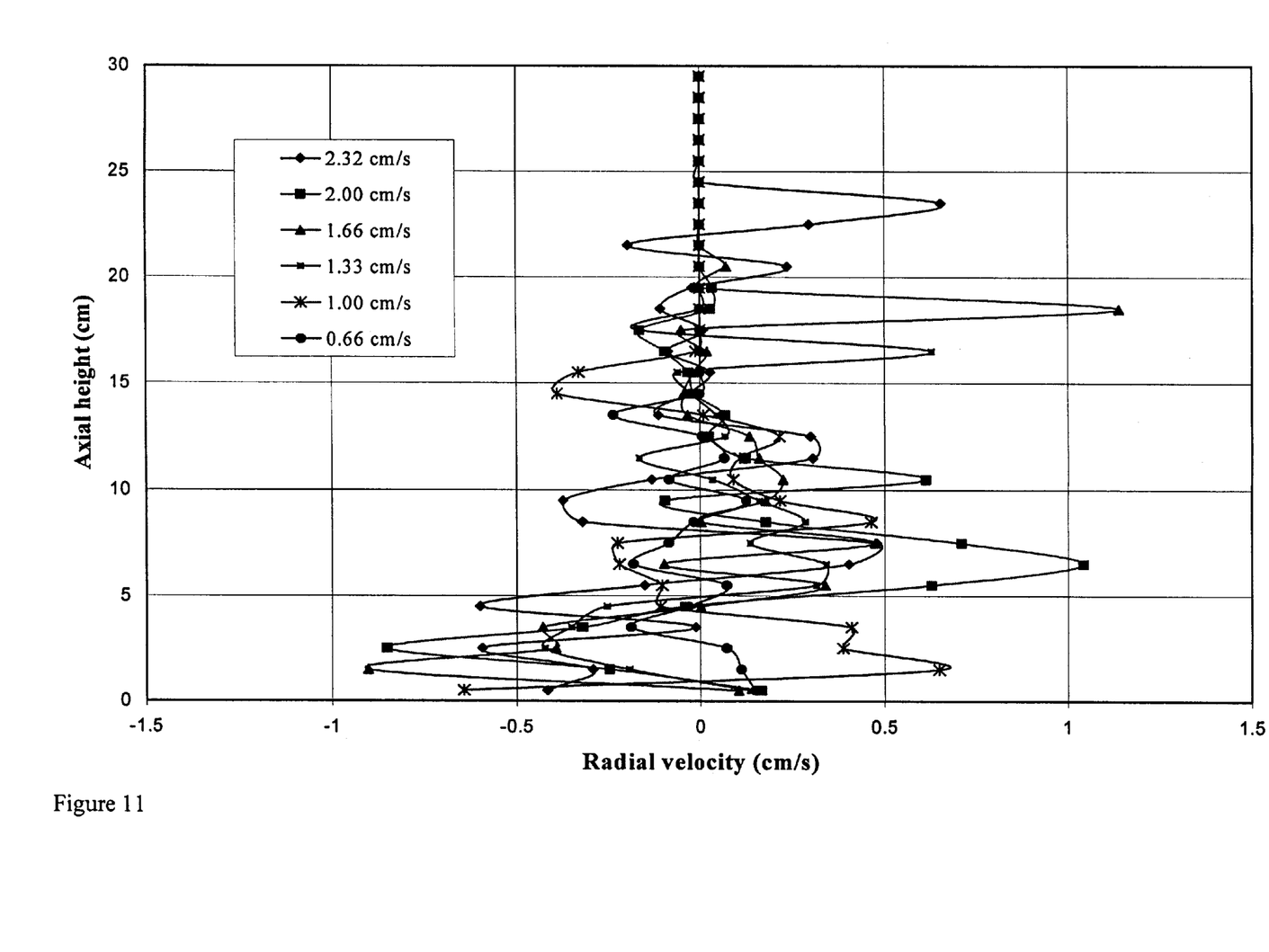
FIG. 11 shows the radial component of particle velocity as a function of bed height.
Figure 12:
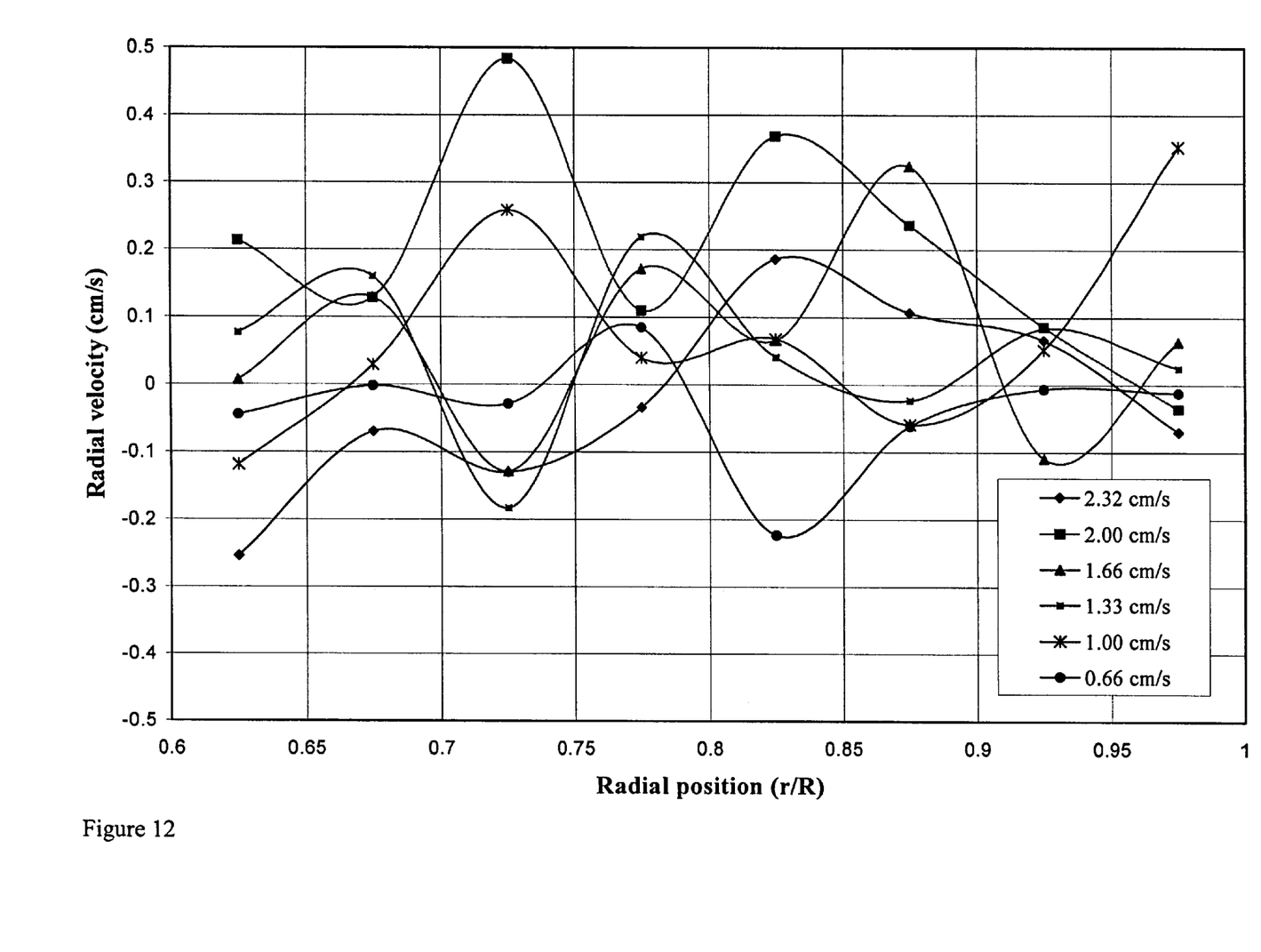
FIG. 12 shows the radial component of particle velocity as a function of radial position.

Further analysis of radioactive particle tracking data provides the radial component of particle velocities as a function of axial and radial position which are presented in FIGS. 11 and 12 respectively. In the former, the radial velocity component is a mean of velocity component in all compartments at the same axial bed height and in the latter case, axial velocity component is a mean of velocity component in compartments equidistant from the centre. It appears that the particle exhibits oscillations in radial velocity in all directions. The magnitude of radial velocity components is lower than axial velocity components indicating that the motion of solid particles in liquid fluidized beds is axially dominant.

Both axial and radial velocity components show no particular trends in axial or radial direction since the bed undergoes smooth fluidization. As may be seen from the PDFs shown in FIG. 7, the particle visits everywhere indicating good mixing characteristics in the bed.

As will be apparent to those skilled in the art, various modifications, adaptations and variations of the foregoing specific disclosure can be made without departing from the scope of the invention claimed herein.

What is claimed is:

1. A method of measuring movement of solid particles and particle interactions in a three-dimensional flowing system, said method comprising the steps of:
   (a) providing at least one radioactive tagged particle within the flowing system;
   (b) providing a first 2-dimensional image receptor capable of detecting the position of the tagged particle in the x-z plane and a second 2-dimensional image receptor capable of detecting the position of the tagged particle in a plane substantially perpendicular to the x-z plane, wherein each of the first and second image receptors are stationary; and
   (c) periodically recording the position of the tagged particle in three dimensions over a length of time.

2. The method of claim 1 wherein the first and second image receptors are gamma cameras.

3. The method of claim 2 wherein the particle is tagged with radioactive technetium.

4. The method of claim 2 further comprising the step of comparing the particle position along one or more of the x, y or z axes against time to determine the particle trajectory.

5. The method of claim 2 further comprising the step of producing a probability distribution function of particle occurrence from the tagged particle occurrence counts within compartments of the flowing system.

6. The method of claim 2 further comprising the step of determining the particle's velocity along one or more of the x, y or z axes over a selected period of time.

* * * * *